United States Patent [19]
Rigterink

[11] 4,148,902
[45] Apr. 10, 1979

[54] N-[(OPTIONALLY SUBSTITUTED PHENYLAMINO)CARBONYL] PYRIDINE CARBOXAMIDES AND INSECTICIDAL USE THEREOF

[75] Inventor: Raymond H. Rigterink, Midland, Mich.

[73] Assignee: The Dow Chemical Company, Midland, Mich.

[21] Appl. No.: 796,647

[22] Filed: May 13, 1977

[51] Int. Cl.$^2$ .................... A01N 9/22; C07D 213/81; C07D 213/82
[52] U.S. Cl. .................................. 424/266; 424/263; 546/316; 546/323
[58] Field of Search ................... 260/295 E, 295.5 D, 260/553 E; 424/263, 266

[56] References Cited

U.S. PATENT DOCUMENTS 3,748,356  7/1973  Wellinga et al. ................. 260/553 E

OTHER PUBLICATIONS

Kulev et al., "Preparations . . . Activity" Chem. Abst., vol. 73, 1970, parag. 55783v.
Wiley, "The RXN of Amides w/Isocyanates" J. Am. Chem. Soc., 30 C., 71, pp. 1310–1311 (1949).

Primary Examiner—Richard Raymond

[57] ABSTRACT

Novel substituted ((phenylamino)carbonyl) pyridine carboxamides are disclosed. The compounds of the instant invention are useful as insecticides and can be formulated to provide insecticidal compositions.

40 Claims, No Drawings

N-[(OPTIONALLY SUBSTITUTED PHENYLAMINO)CARBONYL] PYRIDINE CARBOXAMIDES AND INSECTICIDAL USE THEREOF

BACKGROUND OF THE INVENTION

Substituted (phenylamino)carbonyl) benzamides are known in the art as, for example, in U.S. Pat. No. 3,748,356, U.S. Pat. No. 3,450,747 and Belgian Pat. No. 833,288.

DESCRIPTION OF THE INVENTION

The novel compounds of this invention are substituted (phenylamino)carbonyl) pyridine carboxamides of the formula

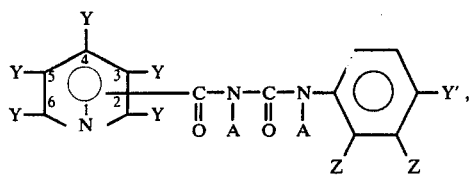

wherein
each Z substituent is individually selected from the group that consists of Cl and H;
each A substituent is individually selected from the group that consists of H and $CH_3$, with the proviso that both A substituents are not $CH_3$;
each Y substituent is individually selected from the group consisting of H, Cl, F and $CH_3$, with the proviso that all of the Y substituents are not H and no more than one Y substituent is $CH_3$; and
Y' represents H, Cl, Br, $CR_3$, $MCR_3$, $C_2R_5$ or $MC_2R_5$, wherein M represents O or S and each R substituent is individually chosen from the group consisting of Cl, F and H.

The term "active ingredients" is at times used hereinafter in this specification to broadly describe the compounds of the present invention.

The active ingredients of the present invention are normally crystalline solids which are of low solubility in water and of moderate solubility in many organic solvents. These active ingredients have low phytotoxicity to plants and have exceptional activity in the kill and control of such undesired insects as the cabbage looper, beet army worm, and the larvae of mosquitoes and hornflies. These active ingredients may be formulated with the usual insecticide carriers, well known to those skilled in the art, to provide insecticidal compositions.

The compounds of the present invention may be prepared via several methods hereinafter set forth. One common method is to react an appropriate pyridine carboxamide with an appropriate substituted phenyl isocyanate in the presence of an organic solvent. The following reaction scheme illustrates this method of preparing the compounds of the present invention:

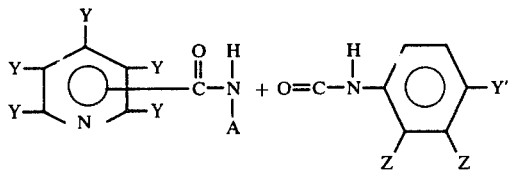

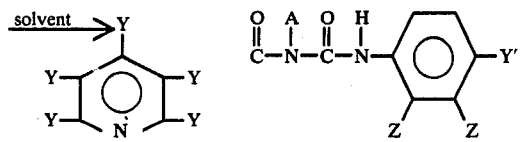

wherein Y, Y', A and Z are as set forth above.

The reaction is carried out by contacting the reactants together in equimolar proportions in the presence of a solvent at a reaction temperature which, at atmospheric pressure, may vary from 0° C. to the boiling point of the solvent used. Examples of suitable solvents are aromatic hydrocarbons such as benzene or xylene, chlorinated hydrocarbons such as chloroform, methylene chloride or ethylene chloride or other inert solvents such as acetonitrile.

Following the completion of the reaction (generally lasting from 0.5 to 24 hours), the mixture is cooled and the precipitated product is collected by filtration or other suitable techniques. This precipitated product is usually washed with a solvent such as xylene and dried. The resulting product may be further purified by recrystallization from a solvent such as, for example, aqueous acetic acid or other purification procedures.

Compounds of the present invention may also be produced by (a) reacting a compound of the formula

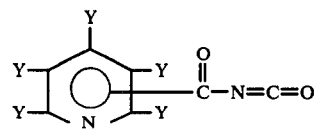

where Y has the aforementioned meaning, with a compound of the formula

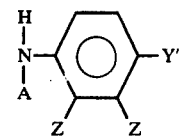

where A, Z and Y' have the aforementioned meanings, in equimolar proportions in the presence of a solvent such as benzene, chloroform or methylene chloride so as to obtain the corresponding compounds of the present invention;

(b) reacting a compound of the formula

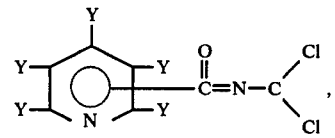

where Y and X have the aforementioned meanings, with a compound of the formula

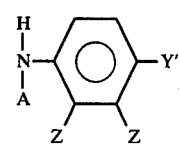

where A, Y' and Z have the aforementioned meanings, in the presence of a suitable solvent such as benzene and toluene and a base such as triethylamine capable of binding the hydrogen chloride involved so as to obtain a compound of the formula

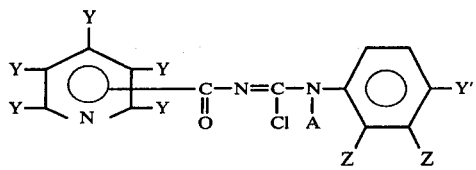

which is then hydrolyzed such as, for example, by agitation in water to thereby obtain the corresponding compound of the present invention;

(c) reacting a compound of the formula

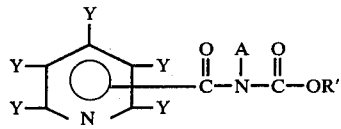

where R' is an alkyl group having from about 1 to about 4 carbon atoms and where Y and A have the aforementioned meanings, with a compound of the formula

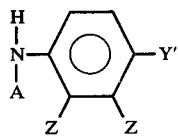

where A, Y' and Z have the aforementioned meanings, in the presence of an inert solvent such as xylene or toluene so as to obtain the corresponding compound of the present invention;

(d) reacting a compound of the formula

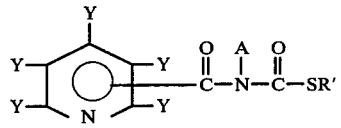

where Y, R' and A have the aforementioned meanings, with a compound of the formula

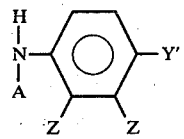

where Y', A and Z have the aforementioned meanings, in equimolar proportions in the presence of a solvent such as toluene so as to obtain the corresponding compound of the present invention.

DESCRIPTION OF SOME PREFERRED EMBODIMENTS

The following examples illustrate the present invention and the manner by which it can be practiced but as such should not be construed as limitations upon the overall scope of the same. The product compounds are identified by elemental analysis and/or nuclear magnetic resonance spectroscopy.

EXAMPLE 1—Preparation of 3,5-dichloro-N-[(4-chlorophenylamino)carbonyl]-4-pyridinecarboxamide A reaction vessel was charged with sixty-eight grams (0.36 mole) of 3,5-dichloro-4-pyridinecarboxamide, 55.5 grams (0.36 mole) of p-chlorophenyl isocyanate, and 1200 milliliters of xylene. The solution was heated under reflux with stirring for three hours. A small amount of impurity was removed by filtering the hot reaction mixture. On cooling in an ice water bath, a solid precipitated. The precipitated product was collected by suction filtration, washed with cold xylene and dried in a vacuum oven at about 70° C. The dried crude product was purified by recrystallization from 90 percent aqueous acetic acid. The yield was 81 grams (66 percent of theoretical) of white needles melting at 225°–227° C. Nuclear magnetic resonance spectral data confirmed the structure as being

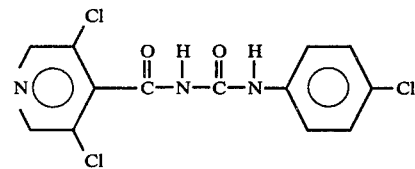

Elemental analysis—Found: 11.81% N. Theory: 12.19% N.

Using a similar method, the compounds of Examples 2–37 were prepared. These compounds and their melting points and/or elemental analysis are set forth in Table 1.

TABLE 1

| Example | Compound | m.p. (° C.) | Found C | Found H | Found N | Theory C | Theory H | Theory N |
|---|---|---|---|---|---|---|---|---|
| 2 | N-(((4-chlorophenyl)amino)-carbonyl)-4-pyridinecarboxamide | 240°–242° | 56.39 | 3.82 | 14.98 | 56.36 | 3.66 | 15.24 |
| 3 | 2,6-Dichloro-N-(((4-chlorophenyl)amino)carbonyl)-4-pyridinecarboxamide | 214°–217° | 46.12 | 2.63 | 12.00 | 45.31 | 2.34 | 12.19 |
| 4 | 3,5-Dichloro-N-(((4-chlorophenyl)amino)carbonyl)-2,6-dimethyl-4-pyridinecarboxamide | 252°–254° | 48.32 | 3.42 | 11.10 | 48.34 | 3.25 | 11.28 |
| 5 | 2,3,5-Trichloro-N-(((4-chlorophenyl)amino)carbonyl)-4-pyridinecarboxamide | 222°–224° | 42.38 | 2.19 | 10.76 | 41.19 | 1.86 | 11.09 |

TABLE 1-continued

| Example | Compound | m.p. (° C.) | Found C | Found H | Found N | Theory C | Theory H | Theory N |
|---|---|---|---|---|---|---|---|---|
| 6 | 2,3,6-Trichloro-N-(((4-chlorophenyl)amino)carbonyl)-4-pyridinecarboxamide | 227°–229° | 42.76 | 2.19 | 10.99 | 41.19 | 1.86 | 11.09 |
| 7 | 2,3,5,6-Tetrachloro-N-(((4-chlorophenyl)amino)carbonyl)-4-pyridecarboxamide | 243°–245° | 39.34 | 1.76 | 9.99 | 37.76 | 1.46 | 10.16 |
| 8 | 3,5-Dichloro-N-(((3,4-dichlorophenyl)amino)carbonyl)-4-pyridinecarboxamide | 222°–224° | — | — | — | 41.18 | 1.85 | 11.09 |
| 9 | 3,5-Dichloro-N-(((4-bromophenyl)amino)carbonyl)-4-pyridinecarboxamide | 225°–249° | — | — | — | 40.12 | 2.06 | 10.80 |
| 10 | 3,5-Dichloro-N-(((2-chlorophenyl)amino)carbonyl)-4-pyridinecarboxamide | 220°–222° | — | — | — | 45.30 | 2.32 | 12.20 |
| 11 | 3,5-Dichloro-N-(((3-chlorophenyl)amino)carbonyl)-4-pyridinecarboxamide | 192°–194° | — | — | — | 45.30 | 2.32 | 12.20 |
| 12 | 3,5-Dichloro-N-(((4-methoxyphenyl)amino)carbonyl)-4-pyridinecarboxamide | 180°–182° | — | — | — | 49.42 | 3.24 | 12.36 |
| 13 | 3,5-Dichloro-N-(((4-methylphenyl)amino)carbonyl)-4-pyridinecarboxamide | 217°–220° | — | — | — | 51.87 | 3.40 | 12.97 |
| 14 | 3,5-Dichloro-N-(((phenyl)amino)carbonyl)-4-pyridinecarboxamide | 187°–189° | — | — | — | 50.35 | 2.93 | 13.55 |
| 15 | N-(((4-chlorophenyl)amino)carbonyl)-3-pyridinecarboxamide | 245°–247° | 56.34 | 3.78 | 15.06 | 56.36 | 3.66 | 15.24 |
| 16 | N-((phenylamino)carbonyl)-3-pyridinecarboxamide | 196°–199° | 64.41 | 4.93 | 18.72 | 64.72 | 4.60 | 17.42 |
| 17 | N-(((4-methylphenyl)aminocarbonyl)-3-pyridinecarboxamide | 211°–213° | 65.82 | 5.34 | 16.23 | 65.87 | 5.13 | 16.46 |
| 18 | N-(((4-methoxyphenyl)amino)carbonyl)-3-pyridinecarboxamide | 168°–171° | 61.76 | 4.85 | 15.57 | 61.98 | 4.83 | 15.49 |
| 19 | N-(((4-methylthiophenyl)amino)carbonyl)-3-pyridinecarboxamide | 215°–218° | 58.55 | 4.52 | 14.29 | 58.52 | 4.56 | 14.62 |
| 20 | N-(((4-nitrophenyl)amino)carbonyl)-3-pyridinecarboxamide | 255°–257° | 54.54 | 3.72 | 19.52 | 54.55 | 3.52 | 19.57 |
| 21 | N-(((3,4-dichlorophenyl)amino)carbonyl)-3-pyridinecarboxamide | 229°–232° | 50.85 | 3.36 | 13.98 | 50.34 | 2.92 | 13.55 |
| 22 | 2-Chloro-N-(((4-chlorophenyl)amino)carbonyl)-3-pyridinecarboxamide | 255°–257° | 50.34 | 3.11 | 13.28 | 50.34 | 2.92 | 13.55 |
| 23 | 2-Chloro-N-(((4-chlorophenyl)amino)carbonyl)-N-methyl-3-pyridinecarboxamide | 124°–126° | 52.16 | 3.68 | 12.80 | 51.87 | 3.42 | 12.96 |
| 24 | 2-Fluoro-N-(((4-chlorophenyl)amino)carbonyl)-3-pyridinecarboxamide | 200°–205° | 53.00 | 3.20 | 14.08 | 53.16 | 3.09 | 14.31 |
| 25 | 4-Chloro-N-(((4-chlorophenyl)amino)carbonyl)-3-pyridinecarboxamide | 210°–220° | 47.09 | 3.57 | 15.17 | 50.34 | 2.92 | 13.55 |
| 26 | 6-Chloro-N-(((4-chlorophenyl)amino)carbonyl)-3-pyridinecarboxamide | 260°–262° | 50.38 | 3.09 | 13.27 | 50.34 | 2.92 | 13.55 |
| 27 | 2-Chloro-N-(((4-chlorophenyl)amino)carbonyl)-6-methyl-3-pyridinecarboxamide | 174°–177° | 51.80 | 3.54 | 12.79 | 51.87 | 3.42 | 12.96 |
| 28 | 2,4-Dichloro-N-(((4-chlorophenyl)amino)carbonyl)-3-pyridinecarboxamide | 174°–178° | 46.16 | 2.76 | 11.85 | 45.31 | 2.34 | 12.19 |
| 29 | 2,6-Dichloro-N-(((4-chlorophenyl)amino)carbonyl)-3-pyridinecarboxamide | 224°–226° | 45.39 | 2.60 | 11.98 | 45.31 | 2.34 | 12.19 |
| 30 | 4,6-Dichloro-N-(((4-chlorophenyl)amino)carbonyl)-3-pyridinecarboxamide | 217°–219° | — | — | — | 45.31 | 2.34 | 12.19 |
| 31 | 2,4-Dichloro-N-(((4-chlorophenyl)amino)carbonyl)-6-methyl-3-pyridinecarboxamide | 180°–182° | 46.82 | 2.95 | 11.52 | 46.89 | 2.81 | 11.72 |

TABLE 1-continued

| Example | Compound | m.p. (°C.) | Found C | Found H | Found N | Theory C | Theory H | Theory N |
|---|---|---|---|---|---|---|---|---|
| 32 | 4,5,6-Trichloro-N-(((4-chlorophenyl)amine)carbonyl)-3-pyridinecarboxamide | 240°–242° | — | — | — | 41.20 | 1.86 | 11.09 |
| 33 | 2,4,5,6-Tetrachloro-N-(((4-chlorophenyl)amino)carbonyl)-3-pyridinecarboxamide | 215°–217° | 37.70 | 1.77 | 10.19 | 37.76 | 1.47 | 10.16 |
| 34 | N-(((4-chlorophenyl)amino)carbonyl)-2-pyridinecarboxamide | 150°–152° | 56.54 | 3.80 | 14.89 | 56.63 | 3.66 | 15.24 |
| 35 | N-(((4-chlorophenyl)amino)carbonyl)-4-methyl-2-pyridinecarboxamide | 177°–179° | 58.04 | 4.32 | 14.13 | 58.04 | 4.18 | 14.50 |
| 36 | 6-Chloro-N-(((4-chlorophenyl)amino)carbonyl)-2-pyridinecarboxamide | 164°–166° | 50.76 | 3.14 | 13.20 | 50.34 | 2.92 | 13.55 |
| 37 | 3,6-Dichloro-N-(((4-chlorophenyl)amino)carbonyl)-2-pyridinecarboxamide | 156°–158° | 45.75 | 2.58 | 11.97 | 45.31 | 2.34 | 12.19 |

EXAMPLE 38—Preparation of 3,5-Dichloro-N-(((4-trifluoromethoxy)phenylamino)carbonyl)-4-pyridinecarboxamide 10.5 Grams (0.052 mole) of 4-(trifluoromethoxy)phenyl isocyanate was added to a mixture of 10 grams (0.052 mole) of 3,5-dichloro-4-pyridinecarboxamide in 200 milliliters of xylene. The resulting mixture was heated under reflux with stirring for 3 hours. This mixture was filtered hot to remove a trace of impurities. On cooling the filtrate in an ice water bath, a solid precipitated. The precipitated solid was collected by suction filtration, washed with cold xylene and dried. The resulting material was recrystallized from 110 milliliters of 90 percent aqueous acetic acid, yielding 7 grams of white needles which were found by nuclear magnetic resonance and elemental analysis to be 1,3-bis(4-(trifluoromethoxy)phenyl)urea. A second precipitate was obtained by adding 100 milliliters of water to the filtrate and cooling. This precipitate was collected by suction filtration, washed with cold xylene and dried. The crude product was recrystallized from 90 percent aqueous acetic acid, yielding 35 grams (17 percent of theoretical) of a white solid. Nuclear magnetic resonance spectroscopy confirmed the product as 3,5-dichloro-N-(((4-(trifluoromethoxy)phenyl)amino)carbonyl)-4-pyridinecarboxamide:

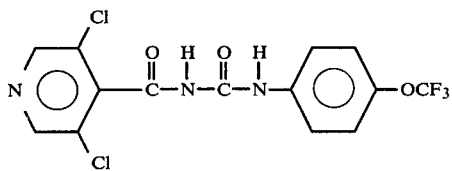

The following representative compounds of the present invention were prepared in general accordance with the above method:

3,5-Dichloro-N-((4-(tetrafluoroethoxy)phenylamino)carbonyl)-4-pyridinecarboxamide;

3,5-Difluoro-N-((4-(trifluoromethoxy)phenylamino)carbonyl)-4-pyridinecarboxamide;

3,5-Dichloro-N-((4-(2,2-dichloro-1,1-difluoroethoxy)phenylamino)carbonyl)-4-pyridinecarboxamide;

3,5-Difluoro-N-((4-(tetrafluoromethoxy)phenylamino)carbonyl-4-pyridinecarboxamide; and 3,5-Difluoro-N-((4-(2,2-dichloro-1,1-difluoroethoxy)phenylamino)carbonyl)-4-pyridinecarboxamide.

PREPARATION OF THE STARTING MATERIALS

Isocyanate starting materials, which are utilized in several of the methods described, can be synthesized by treating the corresponding pyridylcarboxamide with oxalylchloride in the presence of a suitable solvent, e.g. a chlorinated hydrocarbon solvent such as methylene chlorine.

The anisidine starting products which are utilized in several of the described methods are known in the prior art and may be made of the procedure delineated in CA 51:15518C.

The isocyanate starting product utilized in method (b), set forth above, is synthesized by treating the appropriate anisidine or amine with an excess of oxalkylchloride in the presence of a solvent such as carbon tetrachloride. The solvent and excess oxalylchloride may be removed by evaporation.

The compounds of the present invention have been found to be useful in methods for the killing and control of various undesirable agricultural and household insects such as hornflies and houseflies. The compounds are highly active and can be employed to both kill insects outright and/or to prevent adult emergence from juvenile forms of the insect. In such applications, either the insect to be controlled and/or its habitat is contacted or treated with an insecticidal amount of one or more of the compounds of the present invention.

For all such uses, these compounds can be employed in unmodified form. However, the present invention embraces the use of an insecticidally-effective amount of the active ingredients in composition form with a material known in the art as an adjuvant or carrier.

Thus, for example, compositions employing one or a combination of these active ingredients can be in the form of a liquid or a dust; and the adjuvant employed can be any one of a plurality of materials including aromatic solvents, petroleum distillates, water or other liquid carriers, propellant substances, surface-active dispersing agents, light absorbers and finely divided carrier solids.

The exact concentration of one or a combination of the compounds of the present invention in a composition thereof with an adjuvant therefor can vary; it is only necessary that one or a combination of the compounds be present in a sufficient amount so as to make possible the application of an insecticidally effective or inactivating dosage. The activities of the compounds against different insects will vary from compound to compound.

Suitable adjuvants of the foregoing type are well known to those skilled in the art. The methods of applying the solid or liquid insecticidal formulations are well known to the skilled artisan.

The insecticidally-effective dosage desirable for effective use of preparations containing active compounds will naturally depend on various factors such as the active ingredient or ingredients chosen and the form of preparation. Generally, for practical applications, one or a combination of these active ingredients can be broadly applied to the insect larvae or their habitat in compositions containing from about 0.0001 percent to about 98 percent by weight of the compounds.

In the preparation of dust compositions, these compounds can be compounded with any of the finely divided carrier solids such as pyrophyllite, diatomaceous earth, gypsum and the like. In such operations, the finely divided carrier is ground or mixed with one or a combination of the compounds, as active agent(s), or wetted with a solution of the active agent(s) in a volatile organic solvent. Similarly, dust compositions can be compounded with various solid dispersing agents, such as fuller's earth, attapulgite and other clays. These dust compositions can be employed as treating compositions or can be employed as concentrates and subsequently diluted with additional solid dispersing agents or with pyrophyllite, diatomaceous earth, gypsum and the like to obtain the desired amount of active agent in a treating composition. Also such dust compositions can be dispersed in water, with or without the aid of a surfactant, to form spray mixtures.

Furthermore, one or a combination of the compounds or a dust concentrate composition containing such compound(s) can be incorporated in intimate admixture with surface-active dispersing agents such as ionic and nonionic emulsifying agents to form spray concentrates. Such concentrates are readily dispersible in liquid carriers to form sprays containing the toxicant(s) in any desired amount. The choice of the dispersing agent and amount thereof employed are determined by the ability of the agent to facilitate the dispersion of the concentrate in the liquid carrier to produce the desired spray composition.

In the preparation of liquid compositions, one or a combination of the products can be compounded with a suitable water-immiscible organic liquid and surface-active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil soluble and include the nonionic emulsifiers such as the polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene, liquid halohydrocarbons and synthetic organic oils.

An aerosol preparation according to the invention is obtained in the usual manner by incorporating the active substance and a solvent in a volatile liquid suitable for use as a propellant, such as the mixture of chlorine and fluorine derivatives of methane and ethane commercially available under the trademark FREON(R).

Fumigating candles or fumigating powders, i.e. preparations which when burning are capable of emitting a pesticidal smoke, are obtained by taking up the active substance in a combustible mixture which may contain: (a) a sugar or a wood, preferably in ground form, as a fuel, (b) a substance to maintain combustion such as, for example, ammonium nitrate or potassium chlorate and (c) a substance to retard the combustion such as, for example, kaolin, bentonite and/or colloidal silicic acid.

When utilizing the active ingredients of the present invention as insecticides, one or a combination of the active ingredients or a composition containing such is applied to the insects or insect larvae directly, or by means of application to their habitat in any convenient manner, for example, by means of hand dusters or sprayers or by simple mixing with the food to be ingested by the insects or larvae. Application to the foliage of plants is conveniently carried out with power dusters, boom sprayers and fog sprayers. In such foliar applications, the compositions to be employed should not contain any appreciable amounts of any phytotoxic diluents. In large scale operations, dusts or low volume sprays can be applied from an airplane.

In representative activity tests, selected compounds of the present invention were formulated into emulsifiable solutions and added to cups containing water to thereby produce various concentrations of the compounds as the active toxicant in the water. Twenty third-stage larvae of the southern house mosquito, *Culex quinquefasciatus* Say, were added to the water in each cup and incubated at 80° F. until all adults had sufficient time to hatch. An untreated control was also incubated. After one week, all larvae in the control cup had hatched into normal adult mosquitoes. Table 2 sets forth the lowest concentration of each active compound which achieved 100% kill and control of the larvae directly or of the pupae as they began their moult into adults.

The compounds are referred to by their example number.

TABLE 2

| Compoud of Example Number | 1 | 4 | 5 | 21 | 24 | 31 |
|---|---|---|---|---|---|---|
| Lowest Concentration Achieving 100% Kill and Control (ppm) | 0.1 | 1 | 1 | 0.1 | 1 | 1 |

In additional representative activity tests, selected compounds of the present invention were formulated into emulsifiable solutions which were added to cups containing 200 grams of fresh cow manure. The compounds were added to the manure in 5 cubic centimeters of water and stirred thoroughly with a handheld electric mixer. The samples were then seeded with 500 hornfly eggs. The samples were allowed to incubate until all flies had completed their development and had had time to emerge as adults. Percent control was determined by comparison with untreated samples and active compounds were retested until a break point was found. Table 3 sets forth the lowest concentration of each active compound which achieved 100% kill and control of the larvae directly or of the pupae as they began their moult into adults.

TABLE 3

| Compound of Example Number | 1 | 5 | 9 | 22 | 24 | 28 |
|---|---|---|---|---|---|---|
| Lowest Concentration Achieving | 0.1 | 100 | 10 | 1 | 100 | 100 |

TABLE 3-continued

| Compound of Example Number | 1 | 5 | 9 | 22 | 24 | 28 |
|---|---|---|---|---|---|---|
| 100% Kill and Control (ppm) | | | | | | |

In additional representative activity tests, compositions containing selected active ingredients of the present invention were applied to the habitat of beet army worm larvae (Spodoptera exigera). Table 4 sets forth the lowest concentration of each active ingredient, referred to by example number, which achieved 90% kill and control (LC$_{90}$) of the larvae.

TABLE 4

| Compound of Example Number | 1 | 4 | 7 | 8 | 9 | 20 | 25 | 28 | 34 |
|---|---|---|---|---|---|---|---|---|---|
| Lowest Concentration Achieving 90% Kill and Control | 33 | 400 | 400 | 100 | 98 | 400 | 400 | 100 | 400 |

What is claimed is:

1. A compound of the formula

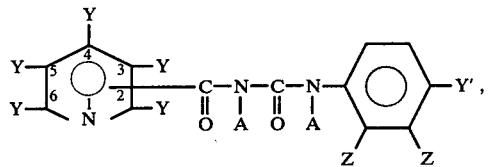

wherein
each Z substituent is individually selected from the group that consists of Cl and H;
each A substituent is individually selected from the group that consists of H and CH$_3$, with the proviso that both A substituents are not CH$_3$;
each Y substituent is individually selected from the group consisting of H, Cl, F and CH$_3$, with the proviso that all of the Y substituents are not H and no more than 1 Y substituent is CH$_3$; and
Y' represents H, Cl, Br, CR$_3$, MCR$_3$, C$_2$R$_5$ or MC$_2$R$_5$, wherein M represents O or S and each R substituent is individually chosen from the group consisting of Cl, F and H.

2. The compound of claim 1 which is 2,6-Dichloro-N-[((4-chlorophenyl)amino)carbonyl]-4-pyridinecarboxamide.

3. The compound of claim 1 which is 3,5-Dichloro-N-[((4-chlorophenyl)amino)carbonyl]-2,6-dimethyl-4-pyridinecarboxamide.

4. The compound of claim 1 which is 2,3,5-Trichloro-N-[((4-chlorophenyl)amino)carbonyl]-4-pyridinecarboxamide.

5. The compound of claim 1 which is 2,3,6-Trichloro-N-[((4-chlorophenyl)amino)carbonyl]-4-pyridinecarboxamide.

6. The compound of claim 1 which is 2,3,5,6-Tetrachloro-N-[((4-chlorophenyl)amino)carbonyl]-4-pyridinecarboxamide.

7. The compound of claim 1 which is 3,5-Dichloro-N-[((3,4-dichlorophenyl)amino)carbonyl]-4-pyridinecarboxamide.

8. The compound of claim 1 which is 3,5-Dichloro-N-[((4-bromophenyl)amino)carbonyl]-4-pyridinecarboxamide.

9. The compound of claim 1 which is 3,5-Dichloro-N-[((2-chlorophenyl)amino)carbonyl]-4-pyridinecarboxamide.

10. The compound of claim 1 which is 3,5-Dichloro-N-[((3-chlorophenyl)amino)carbonyl]-4-pyridinecarboxamide.

11. The compound of claim 1 which is 3,5-Dichloro-N-[((4-methoxyphenyl)amino)carbonyl]-4-pyridinecarboxamide.

12. The compound of claim 1 which is 3,5-Dichloro-N-[((4-methylphenyl)amino)carbonyl]-4-pyridinecarboxamide.

13. The compound of claim 1 which is 3,5-Dichloro-N-[((phenyl)amino)carbonyl]-4-pyridinecarboxamide.

14. The compound of claim 1 which is 2-Chloro-N-[((4-chlorophenyl)amino)carbonyl]-3-pyridinecarboxamide.

15. The compound of claim 1 which is 2-Chloro-N-[((4-chlorophenyl)amino)carbonyl]-N-methyl-3-pyridinecarboxamide.

16. The compound of claim 1 which is 2-Fluoro-N-[((4-chlorophenyl)amino)carbonyl]-3-pyridinecarboxamide.

17. The compound of claim 1 which is 4-Chloro-N-[((4-chlorophenyl)amino)carbonyl]-3-pyridinecarboxamide.

18. The compound of claim 1 which is 6-Chloro-N-[((4-chlorophenyl)amino)carbonyl]-3-pyridinecarboxamide.

19. The compound of claim 1 which is 2-Chloro-N-[((4-chlorophenyl)amino)carbonyl]-6-methyl-3-pyridinecarboxamide.

20. The compound of claim 1 which is 2,4-Dichloro-N-[((4-chlorophenyl)amino)carbonyl]-3-pyridinecarboxamide.

21. The compound of claim 1 which is 2,6-Dichloro-N-[((4-chlorophenyl)amino)carbonyl]-3-pyridinecarboxamide.

22. The compound of claim 1 which is 4,6-Dichloro-N-[((4-chlorophenyl)amino)carbonyl]-3-pyridinecarboxamide.

23. The compound of claim 1 which is 2,4-Dichloro-N-[((4-chlorophenyl)amino)carbonyl]-6-methyl-3-pyridinecarboxamide.

24. The compound of claim 1 which is 4,5,6-Trichloro-N-[(4-chlorophenyl)amino)carbonyl]-3-pyridinecarboxamide.

25. The compound of claim 1 which is 2,4,5,6-Tetrachloro-N-[((4-chlorophenyl)amino)carbonyl]-3-pyridinecarboxamide.

26. The compound of claim 1 which is 6-Chloro-N-[((4-chlorophenyl)amino)carbonyl]-2-pyridinecarboxamide.

27. The compound of claim 1 which is 3,6-Dichloro-N-[((4-chlorophenyl)amino)carbonyl]-2-pyridinecarboxamide.

28. The compound of claim 1 which is 3,5-Dichloro-N-[(4-(tetrafluoroethoxy)phenylamino)carbonyl]-4-pyridinecarboxamide.

29. The compound of claim 1 which is 3,5-Difluoro-N-[(4-(trifluoromethoxy)phenylamino)carbonyl]-4-pyridinecarboxamide.

30. The compound of claim 1 which is 3,5-Dichloro-N-[(4-(2,2-dichloro-1,1-difluoroethoxy)phenylamino)-carbonyl]-4-pyridinecarboxamide.

31. The compound of claim 1 which is 3,5-Difluoro-N-[(4-(tetrafluoroethoxy)phenylamino)carbonyl]-4-pyridinecarboxamide.

32. The compound of claim 1 which is 3,5-Difluoro-N-[(4-(2,2-dichloro-1,1-difluoroethoxy)phenylamino)-carbonyl]-4-pyridinecarboxamide.

33. The compound of claim 1 which is 3,5-dichloro-N-[(4-chloro-phenylamino)carbonyl]-4-pyridinecarboxamide.

34. The compound of claim 1 which is 3,5-dichloro-N-[((4-trifluoromethoxy)phenylamino)carbonyl]-4-pyridinecarboxamide.

35. The compound which is N-[((4-methoxyphenyl)amino)carbonyl]-3-pyridinecarboxamide.

36. The compound which is N-[((4-methylthiophenyl)amino)carbonyl]-3-pyridinecarboxamide.

37. The compound which is N-[((4-nitrophenyl)amino)carbonyl]-3-pyridinecarboxamide.

38. The compound which is N-[((4-chlorophenyl)amino)carbonyl]-4-methyl-2-pyridinecarboxamide.

39. A composition for the conrol of insects comprising a suitable adjuvant and an insecticidally-effective amount of a compound of the formula

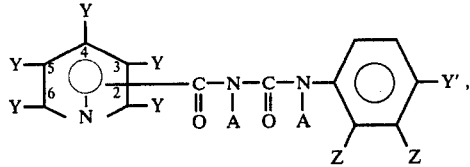

wherein
each Z substituent is individually selected from the group that consists of Cl and H;
each A substituent is individually selected from the group that consists of H and CH$_3$, with the proviso that both A substituents are not CH$_3$;
each Y substituent is individually selected from the group consisting of H, Cl, F and CH$_3$, with the proviso that all of the Y substituents are not H and no more than 1 Y substituent is CH$_3$; and
Y' represents H, Cl, Br, CR$_3$, MCR$_3$, C$_2$R$_5$ or MC$_2$R$_5$, wherein M represents O or S and each R substituent is individually chosen from the group consisting of Cl, F and H.

40. A method of controlling undesired insects which comprises applying to the insects and/or their habitats an insecticidally-effective amount of a compound of the formula

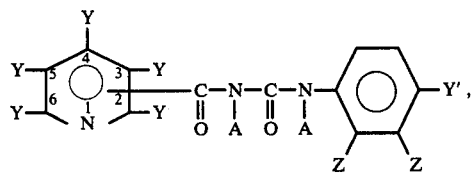

wherein
each Z substituent is individually selected from the group that consists of Cl and H;
each A substituent is individually selected from the group that consists of H and CH$_3$, with the proviso that both A substituents are not CH$_3$;
each Y substituent is individually selected from the group consisting of H, Cl, F and CH$_3$, with the proviso that all of the Y substituents are not H and no more than 1 Y substituent is CH$_3$; and
Y' represents H, Cl, Br, CR$_3$, MCR$_3$, C$_2$R$_5$ or MC$_2$R$_5$, wherein M represents O or S and each R substituent is individually chosen from the group consisting of Cl, F and H.

* * * * *